United States Patent [19]

Hsieh

[11] Patent Number: 5,416,815
[45] Date of Patent: May 16, 1995

[54] ADAPTIVE FILTER FOR REDUCING STREAKING ARTIFACTS IN X-RAY TOMOGRAPHIC IMAGES

[75] Inventor: Jiang Hsieh, Waukesha, Wis.

[73] Assignee: General Electric Company, Milwaukee, Wis.

[21] Appl. No.: 87,568

[22] Filed: Jul. 2, 1993

[51] Int. Cl.⁶ ............... A61B 6/03; G01N 23/083
[52] U.S. Cl. ............................ 378/4; 378/901; 364/413.16
[58] Field of Search ............ 378/4, 901; 364/413.14, 364/413.16

[56] References Cited

U.S. PATENT DOCUMENTS

| | | | |
|---|---|---|---|
| 4,571,635 | 2/1986 | Mahmocdi et al. | 358/510 |
| 4,707,786 | 11/1987 | Dehner | 364/413.21 |
| 5,276,614 | 1/1994 | Heuscher | 364/413.16 |

Primary Examiner—Paul M. Dzierzynski
Assistant Examiner—David Vernon Bruce
Attorney, Agent, or Firm—Quarles & Brady

[57] ABSTRACT

Streaking artifacts in a computed tomography x-ray image are reduced by adaptively filtering each set of projection data. The adaptive filter produces an error vector ($\theta$) by low-pass filtering the projection data (P) and subtracting the error vector ($\theta$) from the projection data (P) prior to image reconstruction. A window function generator controls the low-pass filter as a function of x-ray detector readings.

7 Claims, 2 Drawing Sheets

ADAPTIVE FILTER FOR REDUCING STREAKING ARTIFACTS IN X-RAY TOMOGRAPHIC IMAGES

BACKGROUND OF THE INVENTION

The present invention relates to computed tomography (CT) imaging apparatus; and more particularly, to a method for reducing streaking artifacts caused by limited x-ray photons at certain view angles.

In a computed tomography system, an x-ray source projects a fan-shaped beam which is collimated to lie within an x-y plane of a Cartesian coordinate system, termed the "imaging plane". The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile. The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. The scan data is processed to construct an image that corresponds to a two dimensional slice taken through the object. The prevailing method for reconstructing an image is referred to in the art as the filtered backprojection technique. This process converts the attenuation measurements from a scan into integers called "CT numbers" or "Hounsfield units", which are used to control the brightness of a corresponding pixel on a cathode ray tube display.

A number of factors can contribute to the production of artifacts in the reconstructed image. One of these factors is insufficient x-ray flux due to attenuation of the x-ray beam by the object. For example, bones in the shoulders of a medical patient will highly attenuate x-rays directed horizontally through the chest of the patient and the resulting low x-ray counts at the detectors introduce uncertainty into the acquired view. This uncertainty is manifested as horizontal streaks in the reconstructed image. This uncertainty cannot be reduced by increasing overall x-ray flux density, because this would overload other detector channels receiving less attenuated beams and increase patient x-ray dosage. The streaking cannot be filtered from the image using conventional filters, because such filters reduce image resolution and they are ineffective due to the severity of the streaking artifacts.

SUMMARY OF THE INVENTION

The present invention is an improvement for a computed tomography system, and particularly, a filter for removing streaking artifacts without significantly reducing image resolution. More specifically, the computed tomography system includes: a data acquisition system for acquiring a plurality of views of an object, each view containing a set of x-ray scan data indicative of the number of detected x-ray photons passing through the object; a preprocessor for receiving each view of acquired x-ray scan data and producing corresponding projection data; an adaptive filter for receiving each view of acquired x-ray scan data and each corresponding set of projection data and producing an error vector therefrom; correction means for subtracting the error vector from its corresponding set of projection data; and means for reconstructing an image from the corrected sets of projection data.

A general object of the invention is to reduce streaking artifacts in x-ray tomographic images without reducing image resolution. Streaking artifacts are caused by the increased variance in detector readings resulting from low x-ray flux. Such low x-ray flux readings occur when the x-ray beam is highly attenuated, such as when it passes through bone. The resulting uncertain signal level is manifested as a streak in the reconstructed image. The present invention recognizes that a more aggressive filter should be applied to the acquired projection data when the level of the acquired scan data drops to lower levels. The adaptive filter in the present invention thus provides more filtering when the scan data level is low and less filtering when the scan data level is high.

DETAILED DESCRIPTION OF THE INVENTION

Figure 1:
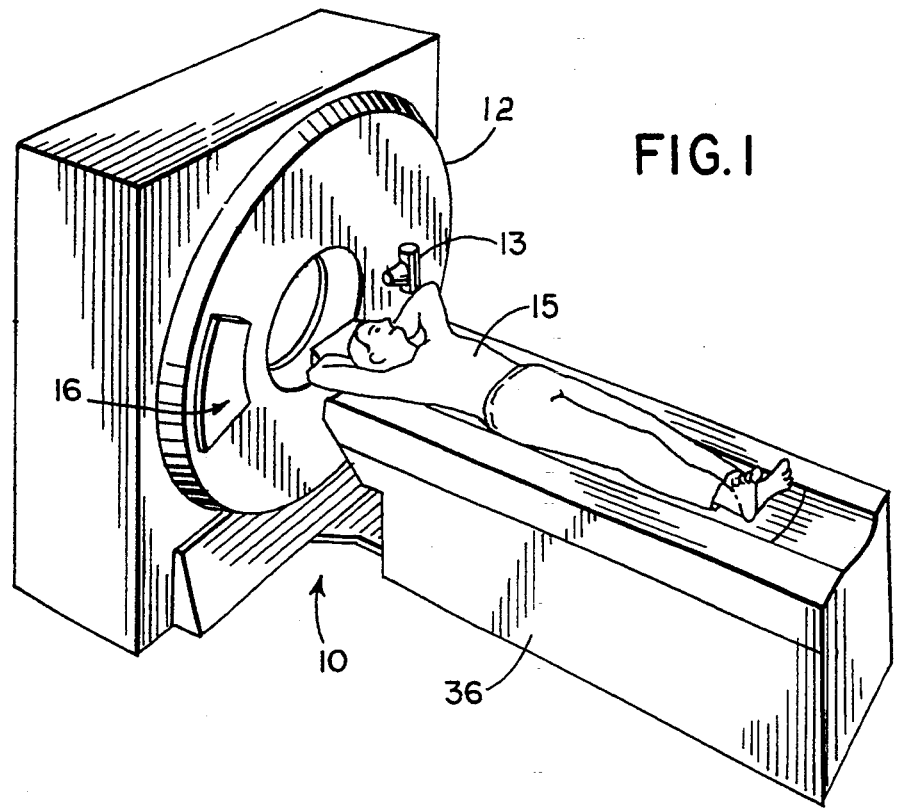
FIG. 1 is a pictorial view of a CT imaging system in which the present invention may be employed.
Figure 2:
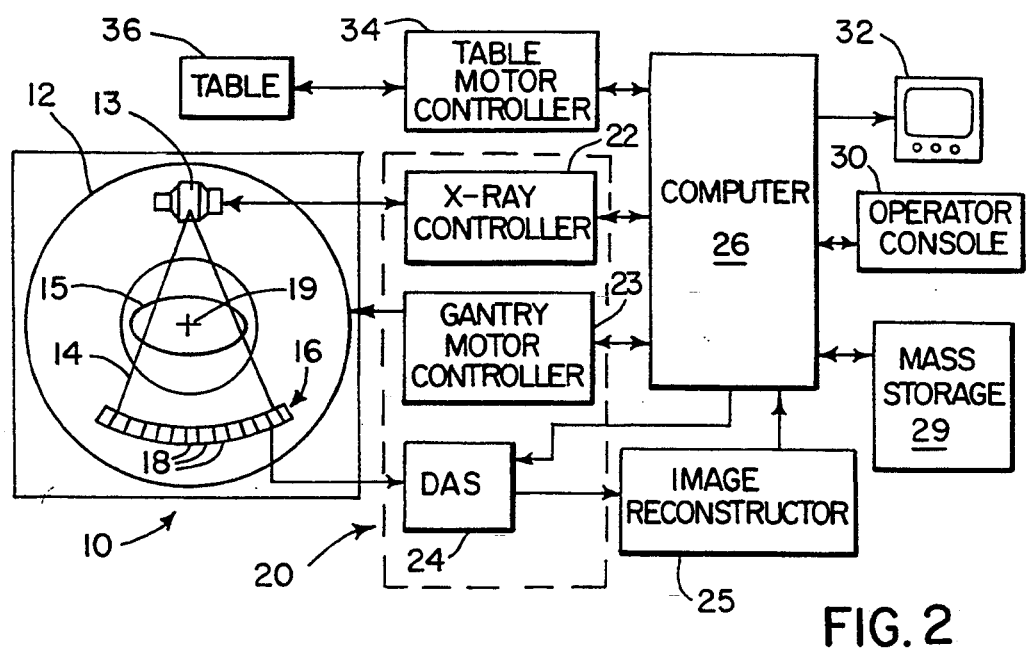
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a fan beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog scan data from detector elements 18 and converts the data to digital signals for subsequent processing. An image reconstructor 25, such as a conventional array processor, receives sampled and digitized x-ray scan data from the DAS 24 and performs high speed image reconstruction as will be described in more detail below. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

During a scan a series of views of the patient is acquired as the gantry 12 rotates about the axis 19. Each view is a set of x-ray scan data values (S) which indicate the number of x-ray photons sensed by the respective detector elements 18. When corrected for offsets, these scan data values can range from negative values to very large positive values. It is a basic teaching of the present invention that this data may be aggressively filtered at points where the values are very low, and virtually unfiltered where the values are high. This "adaptive" filtering is implemented in the image reconstructor 25 which will now be described with reference to FIG. 3.

Figure 3:
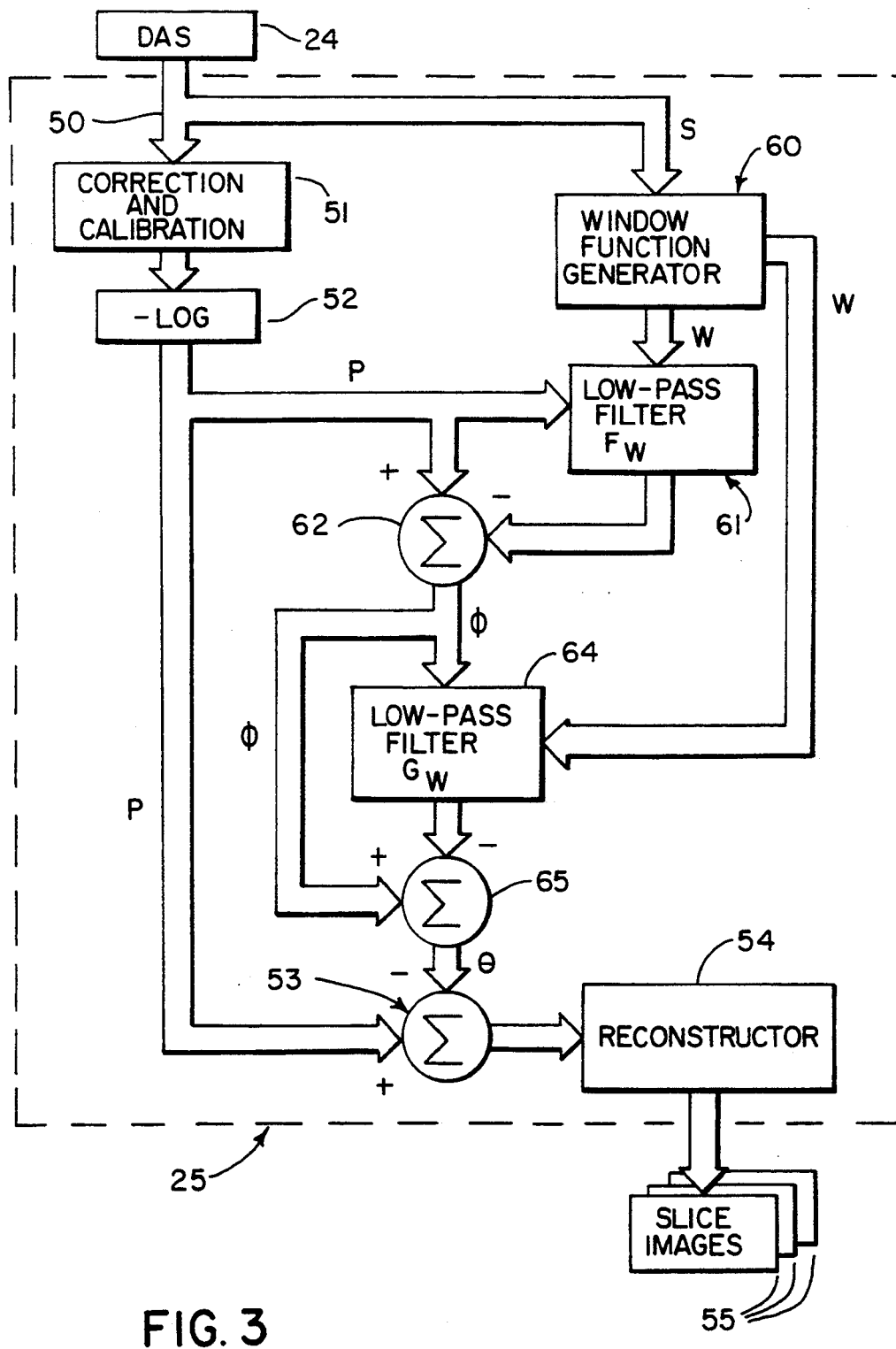
FIG. 3 is a block schematic diagram of the image reconstructor that forms part of the CT imaging system of FIG. 2.

Referring to FIG. 3, each view of scan data is received at input 50 and processed at 51 to correct for various well known errors such as variations in detector and channel gains. The corrected data is next log adjusted at 52 by taking the negative of its logarithm to provide a projection profile P which indicates the amount of attenuating material in the patient 15 along the x-ray beam associated with each detector element 18. It is the fluctuation in these attenuation values at very low detector readings which result in the streaking artifacts, and it is these fluctuations that are removed from the projection profile P by the adaptive filter. As will be described below, the adaptive filter produces an error vector $\theta$ which is subtracted at 53 from the corresponding attenuation values in the projection profile P. The corrected and adaptively filtered projection profiles P are then applied to a reconstructor 54 which backprojects the profiles P to produce slice images 55.

Referring still to FIG. 3, the adaptive filter includes a window function generator 60 which receives the respective views of scan data S as they are produced by the DAS 24. This scan data S is corrected for offset errors, but is otherwise raw data from the detectors 18 indicating the measured x-ray photon counts. The generator 60 compares each scan data value ($S_1$–$S_{852}$) and determines in which of the following regions each value lies:

Region I = $-\infty$ to +4 counts
Region II = +4 to +10 counts
Region III = +10 to +45 counts
Region IV = +45 to +80 counts
Region V = +80 to +$\infty$ counts From this a window function W is produced and used by a first low-pass filter 61 to control the degree of filtering applied to each corresponding attenuation value ($P_1$–$P_{852}$) in the received projection profile P. A first-pass error vector $\phi$ is produced at summing point 62 by subtracting the adaptively filtered projection $F_W(P)$ from the unfiltered projection P:

$$\phi = P - F_W(P). \tag{1}$$

In the preferred embodiment the first low-pass filter 61 is a digital filter known in the art as an "averaging" or "box car" filter, and the number of adjacent values of the input which are averaged together to produce the corresponding filtered output is determined by the window function W. Specifically, all input values indicated as Region I and II are aggressively filtered by averaging 15 adjacent values, all Region III values are filtered by averaging 9 values, all Region IV values are filtered by averaging 3 values, and Region V values are passed through unfiltered. This adaptive filtering may be implemented in a single step in which each projection profile value ($P_1$–$P_{852}$) is separately averaged in accordance with the window function W, or it may be implemented in a process indicated by the following expression:

$$F_W(P) = F_{15}(P)M_1 + F_{15}(P)M_2 + F_9(P)M_3 + F_3(P)M_4 + (P)M_5 \tag{2}$$

where:

$F_{15}$, $F_9$, $F_3$ = respective 15, 9 and 3 point averaging filters;

$M_1$, $M_2$, $M_3$, $M_4$, $M_5$ = respective binary masks which identify the values in respective Regions I, II, III, IV and V.

While the first-pass error vector $\phi$ at the output of summation point 62 can be used directly to adaptively filter the projection profile P, it has been discovered that "object" information is present in the first-pass error vector $\phi$. As a result, shading artifacts are produced in the reconstructed image, particularly around dense objects such as bone. To refine the error vector $\phi$ it is applied along with the window function W to a second low-pass filter 64. A "median" digital filter is employed for this purpose, and the number of neighboring input error vector elements considered by the filter to produce a corresponding output is determined by the window function W. Specifically, for Region I values the input error vector element is passed through unchanged, for Region II values the median of 9 neighboring values is passed, for Region III values the median of 5 neighboring values is passed, for Region IV values the median of 3 neighboring values is passed, and for Region V, the $\phi$ error vector element (i.e. "0") is passed. The output of the second low-pass filter 64 is applied to summing point 65 to produce the final error vector $\theta$:

$$\theta = \phi - G_W(\phi). \tag{3}$$

As with the first low-pass filter 61, the second low-pass filter 64 may be implemented in a single step on each element of the error vector $\phi$, or the binary masks $M_2$–$M_4$ may be used:

$$G_W(\phi) = G_9(\phi)M_2 + G_5(\phi)M_3 + G_3(\phi)M_4. \tag{4}$$

Many variations from the preferred embodiment may be made without departing from the spirit of the invention. Other digital filtering techniques may be employed, and the filters may be applied to the two-dimensional sinogram that includes projection profiles for adjacent views. Thus, rather than averaging or selecting the median value in a long one-dimensional neighborhood of adjacent input elements, the filters (F and G) may use a compact two-dimensional neighborhood centered on the input element to thus filter across adjacent views as well as across adjacent channels. This further improves filter effectiveness without reducing image resolution. Also, the masks $M_1 M_5$ produced by the window function generator 60 may contain high frequency fluctuations because the counts from adjacent channels lie on a boundary between two regions. The performance can be improved by low-pass filtering the masks $M_1$–$M_5$ to remove such fluctuations. And finally, while the range of scan data values has been divided into five regions in order to control the operation of the low-pass filter, any number of regions can be used. Indeed, the number of regions can be increased to the point where the value of the scan data is used to directly control the operation of the low-pass filter.

I claim:

1. A computed tomography imaging system which comprises:

a digital acquisition system for acquiring a set of x-ray scan data (S) whose elements indicate the number of detected x-ray photons passing through an object located in the imaging system;

correction means connected to receive the set of x-ray scan data (S) and being operable to produce a projection profile having corresponding elements which indicate the attenuation of x-rays passing through the object;

an adaptive filter which includes:
  a) a window function generator connected to receive the set of x-ray scan data (S) and being operable to produce a window function (W) which is indicative of the magnitude of each x-ray scan data element;
  b) a low-pass filter connected to receive the projection profile (P) and the window function (W) and being operable to filter each received projection profile element by an amount determined by the window function (W);
  c) subtraction means for producing an error vector by subtracting the filtered projection profile elements produced by the low-pass filter from the corresponding projection profile element; and
  d) means for combining the error vector with the projection profile (P) to produce an adaptively filtered projection profile; and a reconstructor for producing an image from the adaptive filtered projection profiles produced by the adaptive filter.

2. The imaging system as recited in claim 1 in which the low-pass filter is a digital averaging filter and a number of neighboring received projection profile elements indicated by the window function (W) are averaged to produce each filtered projection data element.

3. The imaging system as recited in claim 2 in which the number of neighboring projection profile elements indicated by the window function (W) is inversely related to the magnitude of the corresponding x-ray scan data element.

4. The imaging system as recited in claim 1 in which the adaptive filter includes a second low-pass filter (64) which receives the error vector from the subtraction means and the window function (W) from the window function generator, and is operable to filter elements in the error vector by an amount indicated by the window function (W).

5. The imaging system as recited in claim 4 in which the second low-pass filter is a median digital filter.

6. The imaging system as recited in claim 1 in which the window function generator produces a set of binary masks ($M_1$–$M_5$) that indicate which x-ray scan data elements have magnitudes within selected regions.

7. The imaging system as recited in claim 6 in which each binary mask is low-pass filtered.

* * * * *